US010822581B2

(12) United States Patent
Poon et al.

(10) Patent No.: US 10,822,581 B2
(45) Date of Patent: Nov. 3, 2020

(54) IMMOBILIZED REACTION DEVICE AND A METHOD FOR CARRYING OUT A REACTION BY UTILIZING THE IMMOBILIZATION TECHNOLOGY (71) Applicant: GeneHarbor (Hong Kong) Biotechnologies Limited, Hong Kong (CN)

(72) Inventors: Wing Keung Eric Poon, Hong Kong (CN); Yau Lung Siu, Hong Kong (CN); Junming Chen, Hong Kong (CN); Dong Shen, Hong Kong (CN); Jun Wang, Hong Kong (CN); Liang Sun, Hong Kong (CN)

(73) Assignee: GeneHarbor (Hong Kong) Biotechnologies Limited, Hong Kong (CN)

( * ) Notice: Subject to any disclaimer, the term of this patent is extended or adjusted under 35 U.S.C. 154(b) by 299 days.

(21) Appl. No.: 15/557,616

(22) PCT Filed: Mar. 11, 2016

(86) PCT No.: PCT/CN2016/076142
§ 371 (c)(1),
(2) Date: Sep. 12, 2017

(87) PCT Pub. No.: WO2016/146030
PCT Pub. Date: Sep. 22, 2016

(65) Prior Publication Data
US 2018/0044622 A1    Feb. 15, 2018

(30) Foreign Application Priority Data
Mar. 13, 2015   (CN) .......................... 2015 1 0111592

(51) Int. Cl.
C12M 1/40    (2006.01)
C12P 1/00    (2006.01)
C12M 1/00    (2006.01)
C12P 1/04    (2006.01)
C12M 1/12    (2006.01)
C12P 13/00   (2006.01)
C12M 1/34    (2006.01)
C12P 19/40   (2006.01)

(52) U.S. Cl.
CPC .............. *C12M 21/18* (2013.01); *C12M 1/00* (2013.01); *C12M 1/40* (2013.01); *C12M 25/00* (2013.01); *C12M 25/18* (2013.01); *C12M 29/00* (2013.01); *C12M 29/10* (2013.01); *C12M 41/26* (2013.01); *C12M 41/40* (2013.01); *C12P 1/00* (2013.01); *C12P 1/04* (2013.01); *C12P 13/00* (2013.01); *C12P 13/001* (2013.01); *C12P 19/40* (2013.01)

(58) Field of Classification Search
None
See application file for complete search history.

(56) References Cited

U.S. PATENT DOCUMENTS 7,858,351 B2    12/2010   Fu et al.
8,486,676 B2    7/2013    Jin et al.
2010/0028971 A1  2/2010    Jin et al.

FOREIGN PATENT DOCUMENTS

| CN | 1982445 B | 7/2011 |
| CN | 101134948 B | 12/2011 |
| CN | 102808006 A | 12/2012 |
| CN | 103060554 A | 4/2013 |
| CN | 103146571 A | 6/2013 |
| WO | 2007068173 A1 | 6/2007 |

*Primary Examiner* — Blaine Lankford
(74) *Attorney, Agent, or Firm* — The Webb Law Firm (57) ABSTRACT The present invention provides an immobilized reaction device and a method for carrying out reaction by utilizing the immobilization technology. The immobilized reaction device includes a columnar reactor with an inlet and an outlet. The reactor is provided with an interior cavity which is defined by a top portion and a bottom portion opposite to each other, and a side wall connecting the top portion and the bottom portion.

16 Claims, 1 Drawing Sheet

Specification includes a Sequence Listing.

IMMOBILIZED REACTION DEVICE AND A METHOD FOR CARRYING OUT A REACTION BY UTILIZING THE IMMOBILIZATION TECHNOLOGY

CROSS-REFERENCE TO RELATED APPLICATIONS

This application is the United States national phase of International Application No. PCT/CN2016/076142 filed Mar. 11, 2016, and claims priority to Chinese Patent Application No. 201510111592.9 filed Mar. 13, 2015, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1707773_ST25.txt. The size of the text file is 1,156 bytes, and the text file was created on Sep. 12, 2017.

FIELD OF THE INVENTION

The present invention belongs to the field of bioengineering, and specifically relates to an immobilized reaction device and a method for carrying out a reaction by utilizing the immobilization technology.

BACKGROUND

It is a common technical in the art for producing various chemicals by enzyme, with the advantages of low energy consumption and green technology. However, the liquid enzyme has a limitation: single usage. Therefore, the cost of enzyme in the entire production often occupies a high proportion, which is the main reason for the high cost of enzymatic production. In addition, huge consumption of liquid enzyme violates the principal of green technology. More often, the liquid enzyme itself is another residual in the reaction solution, and such manner can raise the difficulty on product purification. In order to resolve the limitation and disadvantages of liquid enzymes' application, the replacement with immobilized enzyme and immobilized cell can avoid the above defects.

The Chinese patent CN 1982445b discloses a method for preparing a novel immobilized enzyme/cells and a carrier. The carrier has the advantages of providing extended specific surface area, enhancing stability in physical and chemical properties, and high enzyme capacity. However, this invention does not provide a reaction device or a method for industrial production by using the immobilized enzyme or immobilized cells of the type.

SUMMARY OF THE INVENTION

In order to solve the problems existing in the prior art, the invention provides an immobilized reaction device and a method for carrying out a reaction by utilizing the immobilization technology In particular, this invention provides:

(1) An immobilized reaction device comprises a columnar reactor with an inlet and an outlet and provided with an interior cavity which is defined by a top portion, a bottom portion and a side wall connecting the top portion and the bottom portion, wherein the immobilized reaction device is characterized in that a carrier immobilized with enzyme or cells is filled within the interior cavity to form a column body, wherein the column body has a side surface opposite to the side wall of the reactor and there is essentially no gap between the side surface of the column body and the side wall of the reactor.

(2) The immobilized reaction device according to (1), wherein the reactor is capable of allowing a reaction fluid to pass through the reactor at a flow rate up to 100 V/min, while the fluid pressure difference between the inlet and the outlet of the reactor to be maintained at equal or less than 0.3 MPa, wherein V represents the volume of the interior cavity of the reactor.

(3) The immobilized reaction device according to (1), wherein the ratio of the height of the column body to the height of the interior cavity is (0.3-1.0):1.

(4) The immobilized reaction device according to (1), wherein the carrier is a porous organic foam material with open pores, and the shape of the carrier includes granular, block, columnar shape, sheet or strip.

(5) The immobilized reaction device according to (1) or (4), wherein the carrier has natural water wetting rate of at least 0.2 mm/s.

(6) The immobilized reaction device according to (1), wherein the reactor further comprises water-absorbing expansible material or water-impermeable material clamped between the side surface of the column body and the side wall of the reactors such that there is essentially no gap between the side surface of the column body and the side wall of the reactor.

(7) The immobilized reaction device according to (1), wherein the immobilized reaction device further comprises a reaction control tank and a circulation loop is formed between the reaction control tank and the reactor.

(8) The immobilized reaction device according to (7), wherein the lower end of the reactor is provided with an inlet, and the upper end of the reactor is provided with an outlet;

the lower end of the reaction control tank is provided with an outlet, and the upper end of the reaction control tank is provided with an inlet; and the outlet of the reaction control tank is in communication with the inlet of the reactor, and the outlet of the reactor is in communication with the inlet of the reaction control tank.

(9) The immobilized reaction device according to (1), wherein the immobilized reaction device further comprises a pump capable of providing a fluid flow rate in the range of 0.01 V/min to 100 V/min, wherein V represents the volume of the interior cavity of the reactor.

(10) The immobilized reaction device according to (1), wherein the immobilized reaction device further comprises a pH adjusting device.

(11) The immobilized reaction device according to (1), wherein the aspect ratio of the interior cavity of the reactor is (0.1-3.0):1.

(12) A method for carrying out a reaction by using immobilized enzyme or immobilized cell, characterized in that the method carries out a reaction by using the immobilized reaction device according to any one of (1)-(11).

(13) The method according to (12), wherein the method further comprises allowing a reaction fluid to passed through the reactor at a flow rate in the range of 0.01 V/min to 100 V/min, wherein V represents the volume of the interior cavity of the reactor.

(14) The method according to (12) or (13), wherein the hydraulic pressure at the inlet of the reactor is in the range of more than 0 MPa to 0.3 MPa, and the reaction fluid has a pressure difference between the inlet and the outlet of the reactor of less than or equal to 0.3 MPa.

(15) The method according to (12), wherein the pH value of the reaction fluid is 2-12.

(16) The method according to (12), wherein the immobilized enzyme is selected from creatine kinase and S-adenosylmethionine synthetase.

(17) The method according to (12), wherein the immobilized cell is *Escherichia coli*.

Compared with the prior art, the present invention has the following advantages and positive effects:

1. The immobilized reaction device of the present invention adopts an reactor with integrated design, that is, a carrier immobilized with enzyme or cells is filled within the interior cavity of the reactor to form a column body, wherein the column body has a side surface opposite to the side wall of the reactor and there is essentially no gap between the side surface of the column body and the side wall of the reactor. Such design exerts the permeability of the immobilized enzyme or immobilized cells, sufficiently, and thereby the sufficient contact between the reaction solution and the immobilized enzyme or immobilized cells can be achieved.

2. The immobilized reaction device of the present invention can maintain a lower pressure difference in the reactor even when the flow rate is high. Therefore, a high pressure against the immobilized enzyme or immobilized cells during the industrial production can be avoid. Thus, the invention is suitable for industrial scale-up production.

3. During the reaction of the immobilized enzyme or cells by using the immobilized reaction device of the present invention, the reaction fluid flows repeatedly in the longitudinal direction of the reactor, thereby further improving the contact of the immobilized enzyme or the immobilized cells with the reaction solution.

BRIEF DESCRIPTION OF THE DRAWINGS

1. High-flow water pump; 2. Reactor; 3. Reaction control tank; 4. pH adjusting device; 5. Stirring device; 6. pH detection electrode; 7. pH regulation tank

DESCRIPTION OF THE PREFERRED EMBODIMENT

The invention is further described below with reference to the description of specific examples and with reference to the accompanying drawings, which are not to be construed as limiting the invention. Various modifications or improvements may be made by those skilled in the art in light of the basic idea of the invention, but all of them are falling within the scope of the invention without departing from the basic idea of the invention.

The invention provides an immobilized reaction device comprising a columnar reactor with an inlet and an outlet and provided with an interior cavity which is defined by a top portion, a bottom portion and a side wall connecting the top portion and the bottom portion, wherein the immobilized reaction device is characterized in that a carrier immobilized with enzyme or cells is filled within the interior cavity to form a column body, wherein the column body has a side surface opposite to the side wall of the reactor and there is essentially no gap between the side surface of the column body and the side wall of the reactor.

In the immobilized reaction device of the present invention, the carrier used for immobilizing enzyme or cells can be a porous organic foam material with open holes. Therefore, the interior of the carrier also has open holes, i.e., the holes are not closed, and at least two mutually communicated holes are formed inside the carrier. With such carrier, the column body formation also has a three-dimensional grid structure with open holes, which allows the reaction fluid flowing through the interior of the column body. Therefore, the contact area between the reaction fluid and the immobilized enzyme/cells can be remarkably improved.

The shape of the carrier includes granular, block, columnar shape, sheet or strip. When the carrier immobilized with enzyme/cells is installed into the interior cavity of the reactor, it forms a column body. The column body is essentially homogenous, i.e., the density of all parts of the column body is substantially the same. There is, essentially no gap between the side surface of the column body and the side wall of the reactor. That is to say, the reactor of the present invention is designed to be an integration. By such design, the immobilized enzyme or immobilized cells achieves its maximum permeability and thereby can sufficiently contacts and reacts with the reaction fluid during the reaction.

As used herein, the term "essentially no gap" refers that any void of space is not tolerated to the visible inspection. The carrier immobilized with enzyme/cells can be tightly packed, and/or filling the joint or gaps with water-absorbing expansible material or water-impermeable material, in such a manner that there is essentially no gap between the side surface of the column body formed by packing the immobilized enzyme/cells and the side wall of the reactor.

The term "permeability" is the property possessed by immobilized enzyme or immobilized cells, which refers to the ability of reaction fluid passing through the immobilized enzyme or immobilized cells. The permeability reflects the degree of contact between the immobilized enzyme or immobilized cells and the reaction fluid. As the permeability is higher, the contact is better, and therefore, the reaction is improved.

Preferably, the aspect ratio (height-diameter ratio) of the interior cavity of the reactor is (0.1-3.0):1.

The invention relates to the term "aspect ratio" for a reactor, in which, the ratio refers the height of the interior cavity of the reactor versus the diameter of cross section (also referred to as the "inner diameter") of the reactor. The reactor can be prismatic shape (for example, a triangular prism and a quadrangular prism) or cylindrical, preferably cylindrical. In the case that the cross section of the reactor is non-circular, "the diameter of the cross section" is equal to the diameter of equivalent circle, that is, the diameter of a circle which has the same area equal to that of the cross section of the reactor.

The inventor notes that the flow velocity of the reaction fluid is not in consistent throughout the reactor if the aspect ratio of the interior cavity is too small; in contrast, if the aspect ratio is too high, when the reaction fluid passes through the reactor in high flow rate, the pressure difference between the inlet and the outlet of the reactor is too high, as a result, the immobilized enzyme or immobilized cells will undergo excessive pressure in the industrial scale-up production, which is not desired (see comparative example 1). According to the invention, the aspect ratio of the interior cavity of the reactor can be (0.1-3.0):1; preferably, the ratio is (0.3-1.5):1, and more preferably, the ratio is 0.4:1.

Due to the fact that the reactor of the present invention has the above structure and the aspect ratio, as a result, the lower pressure difference can be maintained in the reactor, even in the case of high flow rate, which is important for industrial scale-up production. Therefore, the proposed immobilized reaction device creates conditions for industrial scale-up production.

More specifically, the reaction device of the present invention enables reaction fluid to pass through the reactor with the flow rate up to 100 V/min, while the pressure difference between the inlet and the outlet of the reactor to be maintained less than or equal to 0.3 MPa, wherein V represents the volume of the interior cavity of the reactor (that is, the volume of the reactor). In the present invention, the pressure difference can be determined by measuring the pressure at the inlet and outlet of the reactor with conventional fluid pressure meter.

The material of the reactor is not limited; it can be organic glass, stainless steel, plastic material, enamel and the like, provided that the material does not decompose at pH2-12 and 100° C., and does not react with the reaction solution.

The level of tightness of the carrier immobilized with enzyme or cells within the reactor generally does not affect the pressure difference between the inlet and the outlet of the reactor. The tightness is not limited, as long as not too loose or too tight to induce short circuit or destroy the structure of the carrier.

For example, in the case where a sheet-like carrier immobilized with enzyme/cells is rolled into a cylinder-shaped reel as described below, the level of tightness of the carrier immobilized with enzyme or cells within the reactor can be determined approximately by the following standard:

TABLE 1

| Level of tightness | Description |
| --- | --- |
| level 1 | Gaps can be obvious observed in the reel when the carrier with immobilized enzyme/cells is wound by hand; the width of the gap is more than 1 mm; when it installs into the reactor, the carrier is very loose and the thickness of the carrier is not changed, and there is macroscopic gap between the carrier and the reactor. |
| level 2 | Gaps can be observed in the reel when the carrier with immobilized enzyme/cells is wound by hand; the width of the gap is less than 1 mm; when it installs into the reactor, the carrier is slightly loose and the thickness of the carrier is slightly changed. |
| level 3 | Gaps cannot be visibly observed in the reel when the carrier with immobilized enzyme/cells is wound by hand; the thickness of the carrier is compressed by approximately 0.1 mm when loaded into the reactor. |
| level 4 | Gaps cannot be visibly observed in the reel when the carrier with immobilized enzyme/cells is wound by hand; the thickness of the carrier is compressed by approximately 0.2-0.3 mm when loaded into the reactor. |

The level of tightness of the carrier immobilized with enzyme or cells within the reactor conforms level 2 to 4, and more preferably at level 3.

The carrier used for immobilizing enzyme/cells can be granular or block-shaped. In this case, the column body is formed by stacking the carrier immobilized with enzyme or cells from top to the bottom.

The carrier used for immobilizing enzyme/cells can also be in a columnar shape. In such a case, the column body can be composed of a single carrier immobilized with enzyme/cells or can be formed by stacking groups of carriers immobilized with enzyme/cells together.

The carrier used for immobilizing enzyme/cell can also be in a sheet shape or a strip shape. In such a case, the column body can be a column-shaped reel which is formed by winding a singular sheet/strip-shaped carrier immobilized with enzyme/cells in to cylinder or the identical shape of the column, and can also be a column which is formed by stacking groups of the column-shaped reel as modules. The column-shaped reel is optionally provided with an inner core with a hole-free material, and in this case, it can be understood that the column body can also be a column formed by stacking the sheet-shaped or strip-shaped carriers immobilized with enzyme/cells.

In the present invention, the "side surface" of the column body formed by filling the carrier immobilized with enzyme/cells into the interior cavity refers to the side surface contour of the column body. For example, in the case of the column body disclosed by the invention is composed of a single column-shaped carrier immobilized with enzyme/cells, or is formed by winding a sheet-shaped carrier immobilized with enzyme/cells into a column-shaped reel, said side surface is the side surface of the column-shaped carrier or the column-shaped reel. Due to the fact that the diameter of the column-shaped carrier or the column-shaped reel is substantially equal to the cross-sectional diameter of the reactor, the side surface of the column body is substantially completely attached to the side wall of the reactor. According to the invention, when the column body is formed by stacking sheet-like, strip-shaped, blocky or granular carrier immobilized with enzyme/cells, its side surface refers to the side surface of column stacked by carriers. Due to the fact that the diameter of the column body formed by stacking the carrier is substantially equal to the cross-sectional diameter of the reactor, the side surface of the column body is substantially completely attached to the side wall of the reactor.

In the invention, the interior cavity of reactor can be fully filled with the column body, or a certain space can be reserved at the top and/or the bottom of the interior cavity. Preferably, the ratio of the height of the column body to the height of the interior cavity is (0.3-1.0):1.

The immobilized enzyme or immobilized cells used in the invention can be prepared according to the method described in Chinese patent CN 1982445B, the entire contents of which are incorporated herein by reference. The carrier of the immobilized enzyme/cells is an open porous organic foam material, preferably with the water absorption ability. Open porous provide carrier permeability, so that the reaction fluid can effectively contact with the enzyme molecules or the cells on the carrier during reaction. Open porous is also benefit for mass transfer of the product after enzymatic reaction. The water absorption of the porous material is linearly correlated to its natural water wetting rate. The materials with the natural water wetting rate more than 0.2 mm/s, and preferably more than 0.4 mm/s are ideal candidates for immobilization carrier; the material with the natural water wetting rate less than 0.2 mm/s is not suitable for immobilization carrier. The suitable carrier material comprises, for example, PVA sponge, wood pulp sponge, melamine sponge and the like. The natural water wetting rate can be measured according to the method described in Chinese patent CN 1982445B.

In the present invention, a single carrier immobilized with enzyme/cells or its stacking structure can be sealed and fixed by wrapping material. The wrapping material can be PVA sponge or wood pulp sponge, etc. The carrier itself or wrapping material can have water-absorbing expansible characters so as to prohibit any gap existing between the carrier and the inner wall of the reactor after absorbing water. Alternatively, the gaps may be filled with water impermeable material.

The reaction fluid can react with the immobilized enzyme/cells in one-way flow direction when the reaction is performed with the immobilized reaction device. The fluid circulation direction can be switched as required by inverting the inlet and outlet of the reactor and/or reaction control tank.

Preferably, the immobilized reaction device further comprises reaction control tank. Circulation loop is formed between the reaction control tank and the reactor. The term "circulation loop" refers to a circulation loop that is formed in the direction perpendicular to or parallel to or in any included angle with the horizontal direction. Therefore, the reaction fluid can flow in the circulation loop in clockwise or the anticlockwise direction when the operation of the device, thereby contacting with the immobilized enzyme/cells in singular flow direction.

Preferably, the lower end of the reactor is provided with an inlet, and the upper end is provided with an outlet, or vice versus; the lower end of the reaction control tank is provided with an outlet; the upper end is provided with an inlet. The outlet of the reaction control tank is communicated with the inlet of the reactor, and the outlet of the reactor is communicated with the inlet of the reaction control tank. With this structure, the reaction fluid travels repeatedly from the bottom to the top of the reactor in the longitudinal axis direction, so that the permeability of the immobilized enzyme/cells is further improved.

As used in this context, the term "upper end" and "the lower end" described in reactor or reaction control tank is not necessarily the topmost end or the bottommost end respectively. For example, the upper end of the reactor or the reaction control tank can be any appropriate position which is located 50% above its height, and the lower end can be any appropriate position which is located 50% below its height. In addition, the term "communicate" means that two parts are linked in fluid communication; that is, further parts or devices can be connected between the two parts, as long as the fluid passage can be established in operation.

Figure 1:
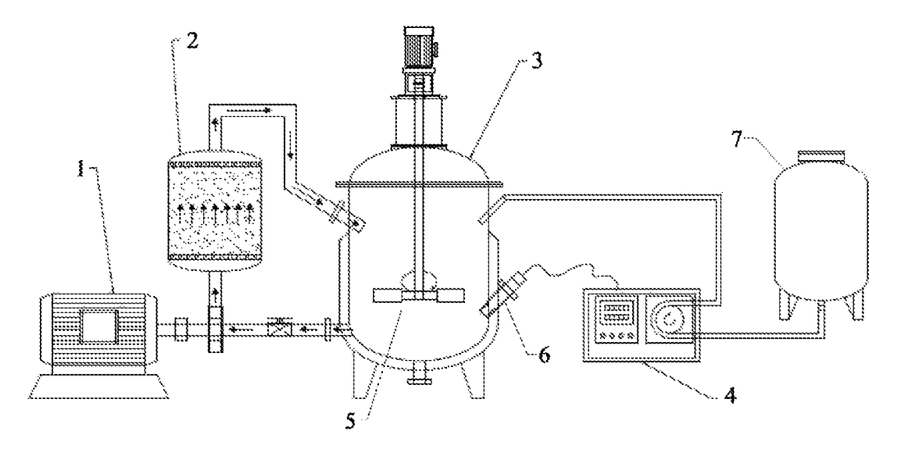
FIG. 1 is a schematic representation showing the structure of an immobilized reaction device according to one embodiment of the present invention; wherein, the reference numbers respectively represent the following components.

As shown in FIG. 1, the reaction control tank can be equipped with stirring device. Preferably, the reaction control tank is also equipped with constant temperature circulating water boiler (not shown in the FIGURE) so as to provide suitable temperature for the reaction fluid. The temperature can be, for example, 4-80° C., preferably 10-70° C. The connection between the reaction control tank and stirring device or constant temperature circulating water boiler can be various conventional manners known in the art. The reaction control tank can be any commercially product available.

Preferably, the immobilized reaction device comprises a pump, such as a high-flow water pump. It can generate a fluid flow rate of 0.01-100 times of the reactor volume per minute, more preferably 0.5 to 20 times of the reactor volume per minute.

As shown in FIG. 1, the high-flow water pump can be connected to the inlet at the lower end of the reactor. The high-flow water pump can pump the reaction fluid in the reaction control tank into the reactor loaded with immobilized enzyme/cells in constant or inconstant flow speed. The connection between high-flow water pump and the reactor can be various conventional manners known in the art. The high-flow water pump can be any commercially product available.

Preferably, the immobilized reaction device further comprises a pH adjusting device in order to monitor the pH value of the reaction fluid in real-time. The pH adjusting device may comprise a pH detecting electrode and pH regulation tank. A portion of the pH detecting electrode (for example the top end) is positioned within the reaction control tank to ensure it securely contact with the reaction fluid to provide the reading of the pH value. The pH regulation tank contains an acid solution or an alkali solution and is connected to the reaction control tank through a pipeline. The pH adjusting device can automatically add acid or base solution as required in order to maintain the desired pH value of the reaction fluid. Preferably, the pH adjusting device can perform adjustment in the range of pH 1-13. The pH adjusting device can be any commercially available product.

The invention further provides a method for carrying out a reaction by utilizing the immobilization technology, wherein the method carries out the reaction by using the immobilized reaction device according to the present invention.

Preferably, the method comprises allowing the reaction fluid passing through the reactor at a flow rate of 0.01-100 times (preferably 0.5-20 times) of the reactor volume per minute, so as to flow circularly between the reactor and the reaction control tank. This can be achieved by using the above high flow water pump.

When the flow rate is 0.01 times of the reactor volume per minute, a large pressure difference will not generate as the flow rate is low. When the flow rate is 100 times of the reactor volume per minute, the above design of the reactor reduces and alleviates the high pressure difference generated so that the reaction product can be produced successfully.

Preferably, the pH value of the reaction fluid is 2-12, and preferably pH 2-11, more preferably pH 5-9. The reaction fluid can comprise with buffer system, such as phosphate buffer solution or Tris. The reaction fluid can also exclude the buffer system upon the requirement in practice.

The reaction utilizing the immobilization technology can be carried out at 4-80° C., preferably at 10-70° C., for example, at 20-40° C., which is adjusted according to the activity temperature of the immobilized enzyme/cells.

When the immobilized reaction device is employed for the reaction, the hydraulic pressure at the inlet of the reactor can reach more than 0 MPa to 0.3 MPa. The hydraulic pressure within this range prohibits the immobilized enzyme/cells from deformed due to excessive pressure. Keeping the reaction device as low pressured is the fundamental key of succeed in industrial scale-up production.

In the method as described, the immobilized enzyme is preferably selected from creatine kinase and s-adenosylmethionine synthetase. The immobilized cell is preferably *Escherichia coli*.

In one specific embodiment of the invention, the method comprises: (a) proper installation of carrier immobilized with enzyme/cells into reactor, wherein the diameter of the reactor and the carrier are matched, and the reactor is a columnar with an aspect ratio of (0.1-3):1; (b) connecting the inlet at the lower end of the reactor to the outlet of the high-flow water pump through a silica gel pipe; connecting the inlet of the water pump to the outlet of the reaction control tank with a pipe; (c) equipping the reaction control tank with stirring device and constant temperature circulating water boiler; (d) installing the pH detecting electrode of the pH regulation device in the reaction control tank, and ensuring the top of the pH detecting electrode can fully contact with the reaction fluid; (e) calibrating the pH adjusting device with pH standard fluid before installation and setting the maximum and minimum pH value and the detection difference value of the regulation range; (f) connecting the outlet at the upper end of the reactor to a flow meter through a pp pipe, and then to the inlet of the reaction control tank; (g) adding a reaction fluid into the reaction control tank and starting the stirring device; setting the stirring mode to be counter-clockwise with the rotational speed of 5-1000 rpm; (h) switching on the high-flow water pump to drive the reaction fluid thru the reaction device and taking reaction fluid from the reaction control tank in real-time manner for product quantitative analysis; upon the amount of the product reaching the predetermined amount, switching off the high-flow water pump to terminating the reaction and switching off the stirring device and the control pump of the pH adjusting device; (i) releasing the reaction fluid from the reaction control tank and replacing with fresh reaction fluid for next batch of reaction;

The contents of the present invention are further explained or illustrated with examples. However, these examples should not be considered as limitations to the present invention.

EXAMPLES

Materials and equipments have used in the examples as below:

Reaction control tank: GeneHarbor (HK) Biotechnologies Ltd. BR-1L;

Adjustable flow type water suction pump: SURGEFLO Ltd. FL-32;

pH regulation device: GeneHarbor (HK) Biotechnologies Ltd. AR-1;

Creatine monohydrate: Jiangsu Yuanyang Pharmaceutical Co. Ltd, China

Disodium adenosine triphosphate: Kaiping Genuine Biochemical Pharmaceutical Co. Ltd, China DL-Methionine: Hubei Huafeng Pharmaceutical Company, China

Example 1: Production of Phosphocreatine

PCR (polymerase chain reaction) primers are designed according to the sequence disclosed by the Chinese patent application No. CN102808006, specifically as follows:

```
Forward primer CPK 1:
5'-GGGAATTCCATATGCCGTTCGGCAACACCCACAAC-3'
(SEQ ID NO: 1)

Reverse primer CPK 2:
5'-CCGCTCGAGCTTCTGCGCGGGGATCATGTCGTCG-3'
(SEQ ID NO: 2)
```

According to the method disclosed by Chinese patent application No. CN102808006, the experiment follows provided procedure: extracting the total RNA from mouse's skeletal muscle and obtain sample's cDNA by RT-PCR. With the cDNA and primers, polymerase chain reaction is performed to obtain creatine kinase gene. The gene is cloned into PET-21a in order to obtain a PET-21 a (+)-CPK, then transfect in to E. coli BL21(DE3).

The strain is inoculated into a 4 mL of LB culture medium (containing 100 ug/ml of ampicillin), and is cultured for 16 hours to serve as primary seed solution. 1% amount of the primary seed solution is further inoculated into a 100 ml of LB culture medium (containing 100 ug/ml of ampicillin) and is cultured (10 hours, 37° C., 200 rpm) as the secondary seed. 1% secondary seed solution is inoculated into a 60 L of LB culture medium (containing 100 ug/ml of ampicillin) in a 100 L of fermentation tank. The fermentation initial conditions are 37° C., 200 rpm in pH7. IPTG is added after 9 hr fermentation to the final concentration is 1 mM, and the fermentation is terminated at 20th hour. The fermentation is harvested by centrifugation at 12,500 rpm in 4° C. for 10 min; 1.12 kg of E. coli cells containing creatine kinase are harvested.

Cells of E. coli which containing creatine kinase are formulated into enzyme solution, and each ml of the enzyme solution contains 0.2 g of cells. Enzyme activity is determined by measuring creatine phosphate according to the Chinese patent application publication no. CN102808006. The enzyme activity is about 6 U/ml.

The immobilized creatine kinase E. coli cell is prepared according to the method disclosed in example 3 of Chinese patent CN1982445B. The carrier has a strip shape with 20 cm long, 5 cm wide, 5 mm thick and 43.6 g weight.

The carrier carried with creatine kinase immobilized E. coli cells is installed into a reactor for immobilized enzyme/immobilized cells. The reactor is a column made of organic glass, which is 7 cm height with the radius of 4.5 cm. The head end and the tail end of the carrier are cut off for about 3 cm by using a knife with 45 degrees of inclination angle. The carrier is then tightly rolled into a homogeneous column body with 5 cm height, 4.5 cm radius and weight of 30 g. The column body is inserted into the reactor with degree of tightness of level 3 described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 3 L/min, and pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2 \cdot 6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into the reaction control tank. Reaction takes place at 37° C. with pH value adjusted at the range from 8.85 to 8.95, and the flow rate of high flow rate water pump at 3 L/min. The enzymatic reaction proceeds for 60 minutes. The pressure difference between the inlet and the outlet of the reactor is 0.08 MPa measured by pressure meter. The final concentration of phosphocreatine is 5 mM.

Example 2: Production of S-adenosylmethionine

PCR (polymerase chain reaction) primers are designed according to the sequence disclosed by the Chinese patent application No. CN101134948B, specifically as follows:

```
Forward primer S1
5'-AGCCTAGGTTAATTAACTTTAAGAAGGAGATACATATGAGAAACATA
ATTGTAAA-3' (SEQ ID NO: 3)

Reverse primer S2
5'-ATAAGCTCAGCGGCGCGCCTTAGAATGTAGTTACTTTTCCTTCA-3'
(SEQ ID NO: 4)
```

According to the method disclosed in Chinese patent CN101134948B, PCR is performed with the DNA of M.

*Jannaschii* ATCC 43067 (ATCC, USA) as substrate. PCR product is digested with Pac I and Asc I and is cloned into pGEMT-EASY (Promega, USA) to obtain plasmid pGEMT-SAM. The recombinant plasmid is transfect into *E. coli* HB101 in order to get strain which expressing S-adenosyl-methionine synthetase.

The strain containing plasmid pGEMT-SAM is inoculated into a 5 mL of LB culture medium (containing 50 mg/L of ampicillin), and is cultured for 16 hours to serve as primary seed solution. 1% primary seed solution is further inoculated to a 100 ml of LB culture medium (containing 50 mg/L of ampicillin) and is cultured (10 hours, 37° C., 200 rpm) as the secondary seed. 1% secondary seed solution is inoculated into a 60 L LB culture medium (containing 100 ug/ml of ampicillin) in a 100 L of fermentation tank. The fermentation initial conditions are 37° C., 200 rpm in pH7, for 40 hour. The fermentation is harvested by centrifugation at 12,500 rpm in 4° C. for 10 min; 1.21 kg of *E. coli* cells which expresses S-adenosylmethionine synthetase are harvested.

According to the method disclosed in Chinese patent CN101134948B, the cells are treated and S-adenosylmethionine synthetase is extracted from the cells in result of 1.78 L of liquid enzyme. The expression amount of S-adenosylmethionine synthetase is approximately 70% (w/w) of total protein production.

The immobilized enzyme of S-adenosylmethionine synthetase is prepared according to the method disclosed in example 3 of Chinese patent CN1982445B. The carrier has a strip shape with 20 cm long, 5 cm wide, 5 mm thick and 20.3 g weight.

The carrier carried with immobilized S-adenosylmethionine synthetase is installed into a reactor for immobilized enzyme/immobilized cells. The reactor is a column made of organic glass, which is 7 cm height with the radius of 4.5 cm. The head end and the tail end of the carrier are cut off for about 3 cm by using a knife with 45 degrees of inclination angle. The carrier is then tightly rolled into homogeneous column body with 5 cm height, 4.5 cm radius and 18 g weight. The column body is inserted into the reactor with degree of tightness of level 3 described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 1 L/min, and pH adjusting device uses 0.5M of NaOH solution for controlling the pH value, and the flow rate of the pump thereof is 1 ml/min.

Reaction solution contains 1.2 g/L of DL-methionine, 4.84 g/L of disodium adenosine triphosphate, 4.1 g/L of $MgCl_2.6H_2O$ and 7.5 g/L of KCl as substrates. Adding 1 L of deionized water and stirring to dissolve after the above substrates are added. After the solution is clear, the pH is adjusted to 7.5 with 2M of NaOH solution.

300 ml of the reaction solution is added into the reaction control tank. Reaction takes place at 58° C. with pH value adjusted at the range from 7.45 to 7.55, and the flow rate of high flow rate water pump at 1 L/min. The enzymatic reaction proceeds for 120 minutes. The pressure difference between the inlet and the outlet of the reactor is 0.08 MPa measured by pressure meter. The final concentration of S-adenosylmethionine is 1 mM.

Example 3

According to the preparation method of Example 1, the creatine kinase gene and the *E. coli* cells expressing the gene are obtained and the fermentation is proceeded. The immobilized *E. coli* cells are prepared on a carrier, which has a strip shape with 22 cm long, 5 cm wide, 5 mm thick and 45.8 g weight.

The carrier carried with immobilized *E. coli* cells is installed into a reactor for immobilized enzyme/immobilized cells. The reactor is a column made of organic glass, which is 1.8 cm height with the radius of 9 cm. The head end and the tail end of the carrier are cut off for about 3 cm by using a knife with 45 degrees of inclination angle. The carrier is then tightly rolled into homogeneous column body with 1.5 cm height, 9 cm radius and 30 g weight. The column body is inserted into the reactor with level 3 of tightness described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 3 L/min, and pH adjusting device uses 0.3M of NaOH solution for controlling the pH value and the flow rate of the pump thereof is 1 ml/min.

Reaction solution contains 8.94 g/L of creatine monohydrate, 12.1 g/L of disodium adenosine triphosphate and 4.1 g/L of $MgCl_2.6H_2O$ as substrates. Adding 1 L of deionized water at about 45° C. and stirring to dissolve after the above substrates are added. After the solution is clear, the pH is adjusted to 8.9 with 2M of NaOH solution.

300 ml of reaction solution is added into a reaction control tank. Reaction takes place at 37° C. with pH value adjusted from 8.85 to 8.95, and the flow rate of high flow rate water pump of 3 L/min. The enzymatic reaction proceeds for 60 minutes. The pressure difference between the inlet and the outlet of the reactor is 0.08 MPa measured by pressure meter. The final concentration of phosphocreatine is 4.7 mM.

Example 4

According to the preparation method of Example 1, the creatine kinase gene and the *E. coli* cells expressing the gene are obtained and the fermentation is proceeded. Immobilized *E. coli* cells are prepared on a carrier, which has a strip shape with 25 cm long, 6 cm wide, 5 mm thick and 48.2 g weight.

Three carriers carried with the immobilized *E. coli* cells are installed into a reactor for immobilized enzyme/immobilized cells. The reactor is a column made of organic glass, which is 16.5 cm height with the radius of 2.8 cm. The head end and the tail end of the carriers are cut off for about 3 cm by using a knife with 45 degrees of inclination angle. The carriers are then tightly rolled into three homogeneous column body respectively, each with 5.5 cm height and 2.8 cm radius, total weight of the three column bodies is 30 g. The three column bodies are inserted into the reactor end to end with degree of tightness of level 3 described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 3 L/min, the pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2.6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into the reaction control tank. Reaction takes place at 37° C. with pH value adjusted from 8.85 to 8.95, and the flow rate of high flow rate water pump of 3 L/min. The enzymatic reaction proceeds for 60 minutes. The pressure difference between the inlet and the outlet of the reactor is 0.09 MPa measured by pressure meter. The final concentration of phosphocreatine is 4.5 mM.

Example 5

According to the preparation method of Example 1, the creatine kinase gene and the *E. coli* cells expressing the gene are obtained and the fermentation is proceeded. Immobilized *E. coli* cells are prepared on a carrier, which has a strip shape with 30 cm long, 5 cm wide, 5 mm thick and 52.4 g weight.

The carrier carried with the immobilized *E. coli* cells is installed into a reactor for immobilized enzyme/immobilized cells. The reactor is a column made of organic glass, which is 3.8 cm height with the radius of 6.2 cm. The head end and the tail end of the carrier are cut off for about 3 cm by using a knife with 45 degrees of inclination angle. The carrier is then tightly rolled into homogeneous column body with 3.7 cm height, 6.2 cm radius and 32 g weight. The column body is inserted into the reactor with level 3 degree of tightness described in table 1. There is no gap between the side wall of the column body and the inner wall of the reactor. Then other device is installed according to FIG. 1, wherein the volume of the reaction control tank is 1 L, the high flow rate water pump is an adjustable flow type water suction pump with the flow rate of 3 L/min, the pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2.6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into the reaction control tank. Reaction takes place at 37° C. with pH value adjusted from 8.85 to 8.95, and the flow rate of high flow rate water pump of 3 L/min. The enzymatic reaction proceeds for 60 minutes. The pressure difference between the inlet and the outlet of the reactor is 0.1 MPa. The final concentration of phosphocreatine is 5.8 mM.

Example 6

According to the preparation method of Example 1, the creatine kinase gene and the *E. coli* cells expressing the gene are obtained and the fermentation is proceeded. Immobilized *E. coli* cells are prepared on a carrier, which has a strip shape with 24 cm long, 5 cm wide, 5 mm thick and 46.5 g weight.

Two carriers carried with the immobilized *E. coli* cell are installed into a reactor for immobilized enzyme/immobilized cells. The reactor is a column made of organic glass, which is 11 cm height with the radius of 3.5 cm. The head end and the tail end of the carriers are cut off for about 3 cm by using a knife with 45 degrees of inclination angle. The carriers are then tightly rolled into two homogeneous column bodies respectively, each with 5 cm height and 3.5 cm radius, total weight of the two column bodies is 34 g. The two column bodies are inserted into the reactor end to end with degree of tightness of level 3 described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 3 L/min, the pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2.6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into a reaction control tank. Reaction takes place at 37° C. with pH value adjusted from 8.85 to 8.95, and the flow rate of high flow rate water pump of 3 L/min. The enzymatic reaction proceeds for 60 minutes. The pressure difference between the inlet and the outlet of the reactor is 0.1 MPa. The final concentration of phosphocreatine is 4.7 mM.

Example 7

According to the preparation method of Example 1, the creatine kinase gene and the *E. coli* cells expressing the gene are obtained and the fermentation is proceeded. Immobilized *E. coli* cells are prepared on a carrier, which has a strip shape with 20 cm long, 5 cm wide, 5 mm thick and 43.6 g weight.

Four carriers carried with the immobilized *E. coli* cell are installed into a reactor for immobilized enzyme/immobilized cells. The reactor is a column made of organic glass, which is 22 cm height with the radius of 2.5 cm. The head end and the tail end of the carriers are cut off for about 3 cm by using a knife with 45 degrees of inclination angle. The carriers are then tightly rolled into four homogeneous column bodies respectively, each with 5 cm height and 2.5 cm radius, total weight of the four column bodies are 30 g. The four column bodies are inserted into the reactor end to end with degree of tightness of level 3 described in table 1. There is no gap between the side wall of the column body and the inner wall of the reactor. Then other devices are installed according to FIG. 1, wherein the volume of the reaction control tank is 1 L, the high flow rate water pump is an adjustable flow type water suction pump with the flow rate of 3 L/min, the pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2.6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into a reaction control tank. Reaction takes place at 37° C. with pH value adjusted from 8.85 to 8.95, and the flow rate of high flow rate water pump of 3 L/min. The enzymatic reaction proceeds for 60 minutes. Since the aspect ratio is too high, the pressure difference between the inlet and the outlet of the reactor is 0.36 MPa. Due to the preference difference is too high, the immobilized cells are extruded and the reaction fluid is unable to fully contact with the immobilized enzyme. The final concentration of phosphocreatine is 0.3 mM.

Comparison Example 1

According to the preparation method of Example 1, the creatine kinase gene and the *E. coli* cells expressing the gene are obtained and the fermentation is proceeded. Immobilized E. coli cells are prepared on a carrier, which has a strip shape with 18 cm long, 5 cm wide, 5 mm thick and 40.4 g weight.

The carriers carried with the immobilized E. coli cell are installed into a reactor for immobilized enzyme/immobilized cells. The reactor is a column made of organic glass, which is 22 cm height with the radius of 2.5 cm. The head end and the tail end of the carriers are cut off for about 3 cm by using a knife with 45 degrees of inclination angle. The carriers are then tightly rolled into four homogeneous column bodies respectively, each with 5 cm height with radius of 2.5 cm, total weight of the four column bodies are 30 g. The four column bodies are inserted into the reactor end to end with degree of tightness of level 1 described in table 1. There is about 1.3 mm width gap existed between the side wall of the column body and the inner wall of the reactor and there are approximately 1 mm width of gaps within the immobilized cells column bodies. Then other devices are installed according to FIG. 1, wherein the volume of the reaction control tank is 1 L, the high flow rate water pump is an adjustable flow type water suction pump with the flow rate of 3 L/min, the pH adjusting device uses 0.3M of NaOH solution for controlling the pH value, and the flow rate of the pump thereof is 1 ml/min.

Reaction solution contains 8.94 g/L of creatine monohydrate, 12.1 g/L of disodium adenosine triphosphate and 4.1 g/L of $MgCl_2 \cdot 6H_2O$ as substrates. Adding 1 L of deionized water at about 45° C. and stirring to dissolve after the above substrates are added. After the solution is clear, the pH is adjusted to 8.9 with 2M of NaOH solution.

300 ml of the reaction solution is added into the reaction control tank. Reaction takes place at 37° C. with pH value adjusted from 8.85 to 8.95, and the flow rate of high flow rate water pump at 3 L/min. The enzymatic reaction proceeds for 60 minutes. The aspect ratio is too high and the pressure difference between the inlet and the outlet of the reactor is 0 MPa. The reaction fluid passes through the gap without sufficient contact with the immobilized cells, and therefore, there is literally no enzymatic reaction proceeded. The final concentration of phosphocreatine is 0.1 mM.

The invention claimed is:

1. An immobilized reaction device comprises a columnar reactor with an inlet and an outlet, wherein the columnar reactor has an interior cavity which is defined by a top portion, a bottom portion and a side wall that connects the top portion and the bottom portion, wherein a carrier immobilized with enzyme or cells is completely filled within the interior cavity of the columnar reactor to form a column body, and the column body has a side surface opposite to the side wall of the reactor and there is essentially no gap between the side surface of the column body and the side wall of the reactor, wherein the carrier has a natural water wetting rate of at least 0.2 mm/s and wherein the aspect ratio of the interior cavity of the reactor is (0.1-3.0):1.

2. The immobilized reaction device according to claim 1, wherein the reactor allows reaction fluid to pass through the reactor at a flow rate up to 100V/min, while the fluid pressure difference between the inlet and the outlet of the reactor maintains at equal or less than 0.3 MPa, wherein V represents the volume of the interior cavity of the reactor.

3. The immobilized reaction device according to claim 1, wherein the ratio of the height of the column body to the height of the interior cavity is (0.3-1.0):1.

4. The immobilized reaction device according to claim 1, wherein the carrier is a porous organic foam material with open pores, and the shape of the carrier includes a columnar shape and sheet.

5. The immobilized reaction device according to claim 1, wherein the reactor further comprises water-absorbing expansible material or water-impermeable material clamped between the side surface of the column body and the side wall of the reactors such that there is essentially no gap between the side surface of the column body and the side wall of the reactor.

6. The immobilized reaction device according to claim 1, wherein the immobilized reaction device further comprises a reaction control tank; and a circulation loop is formed between the reaction control tank and the reactor.

7. The immobilized reaction device according to claim 6, wherein
the lower end of the reactor is provided with an inlet, and the upper end of the reactor is provided with an outlet;
the lower end of the reaction control tank is provided with an outlet, and the upper end of the reaction control tank is provided with an inlet; and
the outlet of the reaction control tank is connected with the inlet of the reactor, and the outlet of the reactor is connected with the inlet of the reaction control tank.

8. The immobilized reaction device according to claim 1, wherein the immobilized reaction device further comprises a pump capable of providing a fluid flow rate in the range of 0.01 V/min to 100 V/min, wherein V represents the volume of the interior cavity of the reactor.

9. The immobilized reaction device according to claim 1, wherein the immobilized reaction device further comprises a pH adjusting device.

10. A method for carrying out a reaction by using immobilized enzyme or immobilized cells, wherein the method carries out a reaction by using the immobilized reaction device according to claim 1.

11. The method according to claim 10, wherein the method further comprises allowing a reaction fluid to passed through the reactor at a flow rate in the range of 0.01 V/min to 100 V/min, wherein V represents the volume of the interior cavity of the reactor.

12. The method according to claim 10, wherein the hydraulic pressure at the inlet of the reactor is in the range of more than 0 MPa to 0.3 MPa, and the reaction fluid has a pressure difference between the inlet and the outlet of the reactor of less than or equal to 0.3 MPa.

13. The method according to claim 10, wherein the pH value of the reaction fluid is 2-12.

14. The method according to claim 10, wherein the immobilized enzyme is selected from creatine kinase and S-adenosylmethionine synthetase.

15. The method according to claim 10, wherein the immobilized cells are *Escherichia coli*.

16. The method according to claim 11, wherein the hydraulic pressure at the inlet of the reactor is in the range of more than 0 MPa to 0.3 MPa, and the reaction fluid has a pressure difference between the inlet and the outlet of the reactor of less than or equal to 0.3 MPa.

* * * * *

```
                       SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: CPK1 forward primer

<400> SEQUENCE: 1
gggaattcca tatgccgttc ggcaacaccc acaac                         35

<210> SEQ ID NO 2
<211> LENGTH: 34
<212> TYPE: DNA
<213> ORGANISM: Artificial Sequence
<220> FEATURE:
<223> OTHER INFORMATION: CPK2 reverse primer

<400> SEQUENCE: 2
ccgctcgagc ttctgcgcgg ggatcatgtc gtcg                          34

<210> SEQ ID NO 3
<211> LENGTH: 55
<212> TYPE: DNA
<213> ORGANISM: Artificial Sequence
<220> FEATURE:
<223> OTHER INFORMATION: S1 forward primer

<400> SEQUENCE: 3
agcctaggtt aattaacttt aagaaggaga tacatatgag aaacataatt gtaaa    55

<210> SEQ ID NO 4
<211> LENGTH: 44
<212> TYPE: DNA
<213> ORGANISM: Artificial Sequence
<220> FEATURE:
<223> OTHER INFORMATION: S2 reverse primer

<400> SEQUENCE: 4
ataagctcag cggcgcgcct tagaatgtag ttactttcc ttca                44
```